(12) United States Patent
Lee et al.

(10) Patent No.: US 9,162,885 B2
(45) Date of Patent: Oct. 20, 2015

(54) GRAPHENE-ENCAPSULATED NANOPARTICLE-BASED BIOSENSOR FOR THE SELECTIVE DETECTION OF BIOMARKERS

(75) Inventors: Ki-Bum Lee, Monmouth Junction, NJ (US); Sung Myung, Highland Park, NJ (US); Aniruddh Solanki, South Plainfield, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 917 days.

(21) Appl. No.: 13/400,021

(22) Filed: Feb. 17, 2012

(65) Prior Publication Data

US 2012/0220053 A1 Aug. 30, 2012

Related U.S. Application Data

(60) Provisional application No. 61/443,950, filed on Feb. 17, 2011.

(51) Int. Cl.
| | |
|---|---|
| *G01N 33/551* | (2006.01) |
| *G01N 33/553* | (2006.01) |
| *B82Y 30/00* | (2011.01) |
| *H01L 29/49* | (2006.01) |
| *H01L 29/786* | (2006.01) |
| *G01N 27/414* | (2006.01) |

(52) U.S. Cl.
CPC ............ *B82Y 30/00* (2013.01); *G01N 27/4146* (2013.01); *H01L 29/4908* (2013.01); *H01L 29/7869* (2013.01); *H01L 29/78696* (2013.01); *G01N 27/4145* (2013.01)

(58) Field of Classification Search
None
See application file for complete search history.

(56) References Cited

U.S. PATENT DOCUMENTS

2013/0040283 A1* 2/2013 Star et al. .................. 435/5

OTHER PUBLICATIONS

Avouris, P., "Graphene: Electronic and Photonic Properties and Devices", Nano Lett. 2010, 10, 4285. Abstract only.
Bradley, K., et al., "Charge Transfer from Absorbed Proteins", Nano Lett. 2004, vol. 4, pp. 253-256.
Byon, H.R., et al., Pseudo 3D Single-Walled Carbon Nanotube Film for BSA-Free Protein Chips: ChemBioChem, Aug. 5, 2005, vol. 6, Issue 8, pp. 1331-1334. Abstract only.
Chen et al., "Noncovalent Sidewall Functionalization of Single-Walled Carbon Nanotubes for Protein Immobilization" J. Am. Chem. Soc., 2001, 123, 3838-3839.
Chen, R.J., et al., "An Investigation of the Mechanisms of Electronic Sensing of Protein Adsorption on Carbon Nanotube Devices", J. Am. Chem. Soc. 2004, 126 (5), pp. 1563-1568. Abstract only.
Cui, Y., et al., "Nanowire nanosensors for highly sensitive and selective detection of biological and chemical species". Science Aug. 2001, 293, (5533) pp. 1289-1292. Abstract only.

(Continued)

*Primary Examiner* — Chris L Chin
(74) *Attorney, Agent, or Firm* — Fox Rothschild LLP

(57) ABSTRACT

A field effect transistor (FET) with a source electrode and a drain electrode distanced apart from each other on a semiconductor substrate, and a gate electrode consisting of a uniform layer of reduced graphene oxide encapsulated semiconductor nanoparticles (rGO-NPs), wherein the gate electrode is disposed between and contacts both the source and drain electrodes. Methods of making and assay methods using the FETs are also disclosed, including methods in which the rGO-NPs are functionalized with binding partners for biomarkers.

20 Claims, 7 Drawing Sheets

(56) References Cited

OTHER PUBLICATIONS

Dong, X., et al., Electrical Detection of DNA Hybridization with Single-Base Specificity Using Transistors Based on CVD-Grown Graphine Sheets, Adv. Mater. Apr. 12, 2010, vol. 22, Issue 14, pp. 1649-1653. Abstract only.

Du, X., et al., "Approaching ballistic transport in suspended graphene". Nat. Nanotechnol. Jul. 20, 2008, 3, pp. 491-495. Abstract only.

Du, D., et al., "Sensitive Immunosensor for Cancer Biomarker Based on Dual Signal an and Multi-Enzyme Functionallized Carbon Nanospheres", Anal. Chem. Apr. 1, 2010, 82, pp. 2989-2995.

Dupont, J., et al., "Preparation of 1-Butly-3-Methly Imidazolium-Based Room Temperature Ionic Liquids", Organic Syntheses, Coll. vol. 10, 2002, 79, p. 236.

Eda, G., et al., "Large-area ultrathin films of reduced graphene oxide as a transparent and flexible electronic material", Nat. Nanotechnol. Apr. 6, 2008, 3, pp. 270-274. Abstract only.

Geim, A.K., et al., "The Rise of Graphene", Nat. Mater. 2007, 6, pp. 183-191. Abstract only.

Jiao, L., et al., "Narrow graphene nanoribbons from carbon nanotubes", Nature 2009, 458, pp. 877-880. Abstract only.

Jung, J.H., et al., "A Graphene Oxide Based Immuno-biosensor for Pathogen Detection", Angew. Chem. Int. Ed. Aug. 2, 2010, vol. 49, Issue 33, pp. 5708-5711. Abstract only.

Kim, K.S., et al., "Large-scale pattern growth of graphene films for stretchable transparent electrodes", Nature Feb. 5, 2009, 457, pp. 706-710. Abstract only.

Li, X. et al., "Large-Area Synthesis of High-Quality and Uniform Graphene Films on Copper Foils", Science, May 7, 2009, vol. 324, No. 5932, pp. 1312-1314. Abstract only.

Lu, J., et al., "Nanometal-decorated exfoliated graphite nanoplatelet based glucose biosensors with high sensitivity and fast response". ACS Nano Sep. 23, 2008, 2, pp. 1825-1832. Abstract only.

Lu, et al., "A graphene platform for sensing biomolecules", Angew. Chem. Int. Ed. 2009, 48, 4785-7. Abstract only.

Mao, S., et al., "Specific Protein Detection Using Thermally Reduced Graphene Oxide Sheet Decorated with Gold Nanoparticle-Antibody Conjugates", Adv. Mater. Aug. 24, 2010, vol. 22, Issue 32, pp. 3521-3526. Abstract only.

Myung, S., et al. "Ambipolar Memory Devices Based on Reduced Graphene Oxide and Nanoparticles", Adv. Mater. May 11, 2010, vol. 22, Issue 18, pp. 2045-2049. Abstract only.

Myung, S., et al., "Large-Scale 'Surface-Programmed Assembly' of Pristine Vanadium Oxide Nanowire-Based Devices", Adv. Mat. Oct. 2005, vol. 17, Issue 19, pp. 2361-2364. Abstract only.

Novoselov, K.S., et al., "Two-dimensional gas of massless Dirac fermions in graphene", Nature, Nov. 10, 2005, 438, pp. 197-200. Abstract only.

Novoselov, K.S., et al., Electric Field Effect in Atomically Thin Carbon Films, Science Oct. 22, 2004, vol. 306, No. 5696, pp. 666-669. Abstract only.

Ohno, Y., et al., "Electrolyte-Gated Graphene Field-Effect Transistors for Detecting pH and Protein Adsorption", Nano Lett. 2009, 9, pp. 3318-3322. Abstract only.

Patolsky, F., et al., "Fabrication of silicon nanowire devices for ultrasensitive, label-free, real-time detection of biological and chemical species", Nature Protocols, 2006, vol. 1, No. 4, pp. 1711-1724.

Shan, C., et al., "Direct Electrochemistry of Glucose Oxidase and Biosensing for Glucose Based on Graphene", Anal. Chem. 2009, 81(6), pp. 2378-2382.

Star, A., et al., "Nanotube Optoelectronic Memory Devices", Nano Letters, 2004, 4 (9), pp. 1587-1591. Abstract only.

Tang, X., et al., "Carbon Nanotube DNA Sensor and Sensing Mechanism", Nano Lett. 2006, 6 (8), pp. 1632-1636. Abstract only.

Woolley, A.T., et al., "Direct haplotyping of kilobase-size DNA using carbon nanotube probes", Nature Biotechnology, 2000, 18, pp. 760-763. Abstract only.

Zhang, Y., et al., "Experimental observation of the quantum Hall effect and Berry's phase in graphene," Nature Nov. 10, 2005, 438, pp. 201-204. Abstract only.

Zheng, G., et al., "Multiplexed electrical detection of cancer markers with nanowire sensor arrays", Nat. Biotechnol. Oct. 23, 2005, 23 (10), pp. 1294-1301. Abstract only.

\* cited by examiner

GRAPHENE-ENCAPSULATED NANOPARTICLE-BASED BIOSENSOR FOR THE SELECTIVE DETECTION OF BIOMARKERS

CROSS-REFERENCE TO RELATED APPLICATION

This application claims the benefit of U.S. provisional application Ser. No. 61/443,950 filed Feb. 17, 2011, the disclosure of which is incorporated herein by reference in its entirety.

STATEMENT REGARDING FEDERALLY FUNDED RESEARCH

The research leading to the present invention was supported in part by NIH New Innovator Award, 2009, Grant No. NIH-1DP20D00646201. Accordingly, the U.S. Government has certain rights in this invention.

BACKGROUND OF THE INVENTION

Nanomaterials, such as silicon nanowires (SiNWs), carbon nanotubes (CNTs), and graphene, have gained much attention for use in electrical biosensors due to their nanoscopic and electrical properties. See, for example, Cui et al., Science 2001, 293, 1289; Patolsky et al. Protoc. 2006, 1, 1711; Bradley et al. Nano Lett. 2004, 4, 253; Chen et al. J. Am. Chem. Soc. 2004, 126, 1563; Star et al., Nano Lett. 2004, 4, 1587; Tang et al., Nano Lett. 2006, 6, 1632; Lu et al., ACS Nano 2008, 2, 1825; and Mao et al., Adv. Mater. 2010, 22, 3521.

For instance, SiNWs and CNTs can be integrated into field-effect transistors (FETs) to detect small amounts of target biomolecules with high sensitivity and selectivity by measuring electrical disturbances induced by the binding of these biomolecules to the surface of the nanostructure. See, for example, Woolley et al., Nat. Biotechnol. 2000, 18, 760; and Zheng et al., Nat. Biotechnol. 2005, 23, 1294. The detection of biomarker proteins with high sensitivity and selectivity is vital for the early diagnosis of many diseases such as cancer and HIV. For this purpose, carbon-based nanomaterials like CNTs and graphene have become attractive for fabricating highly sensitive FET-based biosensors. See, for example, Du et al., Anal. Chem. 2010, 82, 2989; Jung et al., Angew. Chem. Int. Ed. 2010, 49, 5708; Lu et al., Angew. Chem. Int. Ed. 2009, 48, 4785; Ohno et al., Nano Lett. 2009, 9, 3318; and Shan et al., Anal. Chem. 2009, 81, 2378. In particular, the use of graphene in FET-based biosensors is becoming more and more appealing not only due to its unique properties such as higher 2-D electrical conductivity, superb mechanical flexibility, large surface area, and high chemical and thermal stability, but also due to its ability to overcome the limitations of CNTs such as variations in electrical properties of CNT-based devices and the limited surface area of CNTs. See, for example, Avouris, Nano Lett. 2010, 10, 4285; Novoselov et al., Science 2004, 306, 666; Kim et al., Nature 2009, 457, 706; Li et al., Science 2009, 324, 1312; Novoselov et al., Nature 2005, 438, 197; Zhang et al., Nature 2005, 438, 201; Geim et al., Nat. Mater. 2007, 6, 183; Jiao et al., Nature 2009, 458, 877; and Du et al., Nat. Nanotechnol. 2008, 3, 491.

Nevertheless, there have been only a few reports on developing graphene FET-based biosensors, and their potential as biosensors has not been fully explored. See, for example, Dong et al., Adv. Mater. 2010, 22, 1649. It would therefore be desirable to develop nanoscopic graphene-based biosensors that are simple in device structures, small in size, and allow label-free detection and real-time monitoring of biomarkers, all of which are useful criteria for biosensors.

SUMMARY OF THE INVENTION

In one embodiment, the present invention provides a field effect transistor (FET) in which a source electrode and a drain electrode are formed apart from each other on a semi-conductor substrate and a gate electrode incorporating a uniform layer of reduced graphene oxide encapsulated semiconductor nanoparticles (rGO-NPs) is disposed between and contacts both the source and drain electrodes. In another embodiment, the gate electrode is functionalized with a linker molecule having the structure:

X—Y—Z wherein X is a polyaromatic ring structure that bonds non-covalently with the GO-NPs, Y is a spacer moiety selected from alkylene and poly(alkylene oxide) groups containing from 1 to 12 carbon atoms and Z is an omega-functional group capable of reacting with, or being activated to react with, and covalently bonding to an amine. In another embodiment, the omega functional group of the linker molecule is covalently bonded to a polypeptide binding partner for a biomarker. In certain embodiments, the polypeptide binding partner is an antibody, such as a monoclonal antibody.

In another embodiment, the present invention provides a method of making an FET according to the present invention by: a) layering conductive metal electrodes on a semi-conductor substrate; b) layering a patterned photoresist on the substrate and electrodes to define an exposed area for formation of a gate electrode; c) functionalizing the semiconductor and metal electrode surfaces on the exposed area with a self assembled monolayer (SAM) of positively charged amines; d) centrifuging the functionalized substrate in a solution containing graphene oxide-encapsulated semiconductor nanoparticles (GO-NPs) to form a gate electrode on the SAM that is a substantially uniform layer of GO-NPs; e) removing the patterned photoresist; and f) reducing the graphene oxide of the GO-NPs to form rGO-NPs.

In another embodiment, the method further includes the step of providing a linker molecule having the structure:

X—Y—Z wherein X is a polyaromatic ring structure that bonds non-covalently with the GO-NPs, Y is a spacer moiety selected from alkylene and poly(alkylene oxide) groups containing from 1 to 12 carbon atoms and Z is an omega-functional group capable of reacting with, or being activated to react with, and covalently bonding to an amine; and bonding the rGO-NPs of the FET to the polyaromatic ring structure. In another embodiment, the method further includes the step of providing a polypeptide binding partner with a binding region for a biomarker and a non-binding region with a free amino group, and covalently bonding the omega-functional group of the linker molecule to the free amino group of the polypeptide.

In another embodiment, the present invention provides a method of detecting a biomarker in a sample by contacting a FET of the invention that is functionalized with a polypeptide binding partner for the biomarker with the sample, and measuring conductance, wherein a decrease in conductance relative to a control is indicative of the presence of the biomarker in the sample that is bound to the binding partner.

DETAILED DESCRIPTION OF THE INVENTION

Figure 1A:
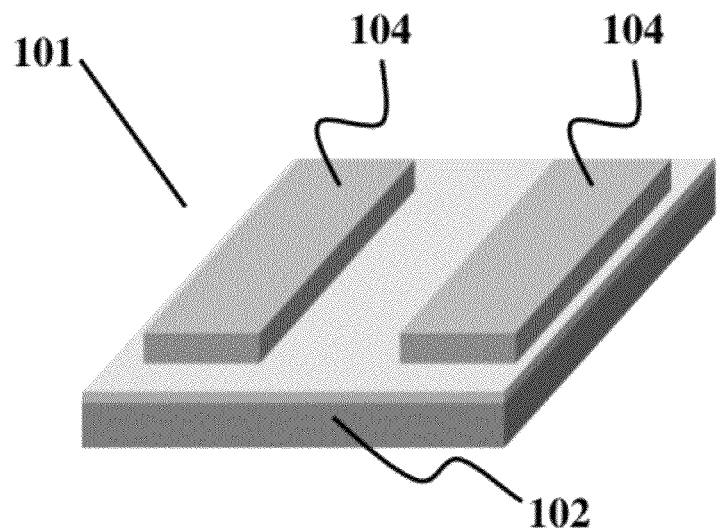
FIGS. 1A-D illustrate an embodiment of a fabrication process of biomolecular sensors according to the present invention.

In one embodiment, the present invention provides a field effect transistor (FET) in which a source electrode and a drain electrode are formed apart from each other on a semi-conductor substrate. A gate electrode incorporating a uniform dense layer of reduced graphene oxide encapsulated semiconductor nanoparticles (rGO-NPs) is disposed between and contacts both the source and drain electrodes.

The semiconductor substrate and semiconductor nanoparticles may be formed from any semiconductor materials suitable for use in FETs. The semiconductor material is preferably a silicon oxide. The source and drain electrodes are conductive metal electrodes. In a preferred embodiment, the source and drain electrodes are gold electrodes.

In another embodiment, the graphene gate is functionalized with a linker molecule. In one embodiment, the linker molecule has the structure:

X—Y—Z wherein X is a polyaromatic ring structure that bonds non-covalently with the GO-NPs, Y is a spacer moiety selected from alkylene and poly(alkylene oxide) groups containing from 1 to 12 carbon atoms and Z is an omega-functional group capable of reacting with, or being activated to react with, and covalently bonding to an amine. Polyaromatic ring structures suitable for use with the present invention include the structures found in polyaromatic hydrocarbons such as pyrene, anthracene, phenanthrene, benzopyrene, coronene, triphenylene, and the like. Pyrene is typically used.

The spacer moiety, Y, is typically an alkylene group containing from three to six carbon atoms, and more typically is a butylene group. The spacer can also be a polymer oligomer containing no more than 18 carbon atoms. The omega functional group is a moiety capable of reacting with and covalently bonding to a peptide amine, or capable of being activated to react and form such a bond. Therefore, Z is preferably an aldehyde, ketone or carboxylic acid group.

Linker molecules that contain polyaromatic hydrocarbon moieties that interact with graphene by pi-stacking, and methods for functionalizing graphene with such linkers, are known in the art and disclosed, for example, by Byon et al., ChemBioChem, 2005, 6, 1331 and Chen et al., J. Am. Chem. Soc., 2001, 123, 3838. Examples of linker compounds with the X—Y—Z structure that are suitable for use with the present invention include 4-(pyren-1-yl)butanal and 1-pyrene-butanoic acid, succinimidyl ester.

Biotinylated linker compounds can also serve as the linker molecule. Biotinylated compounds that non-covalently bond with graphene include biotin-coupled triton/PEG and PEI/biotin-coupled PEG. Instead of being covalently bonded to a peptide amine by the omega-functional group of an X—Y—Z structure linker compound, biotinylated linkers are subsequently bound to peptide-streptavidin conjugates.

The polypeptide binding partner to which the linker molecule is covalently bonded or bound is any polypeptide that contains a primary or secondary amine and is capable of selectively binding to a biomarker of interest. The polypeptide binding partner may be, for example, a protein, polypeptide, peptide, antigen, antibody, or an antibody fragment. In a preferred embodiment, the polypeptide binding partner is an antibody, preferably a human antibody, and preferably a monoclonal antibody.

The biomarker may be any biomarker of interest that is capable of selectively binding to a polypeptide binding partner. The biomarker may be, for example, a protein, polypeptide, peptide, antigen, or antibody. In a preferred embodiment, the biomarker is a cell surface marker expressed in a cancer cell, for example HER2 or EGFR.

The polypeptide binding partner is covalently bonded to the omega functional group of the X—Y—Z linker compound by conventional techniques. When Z is a carboxylic acid group, a covalent amide bond with an amine of the binding partner can be formed by known carbodiimide-mediated coupling reactions. When Z is an aldehyde or ketone, a covalent bond with the amine can be formed by conventional reductive animation reactions.

The polypeptide binding partner can also be conjugated to streptavidin and subsequently bound to a biotinylated linker molecule.

In another embodiment, the present invention provides a method of making an FET according to the present invention by a) layering conductive metal electrodes on a semiconductor substrate; b) layering a patterned photoresist on the substrate and electrodes to define an exposed area for formation of the gate electrode; c) functionalizing the semiconductor and conductive metal surfaces on the exposed areas with a self assembled monolayer (SAM) of positively charged amines; d) centrifuging the functionalized substrate in a solution containing graphene oxide-encapsulated semiconductor nanoparticles (GO-NPs) to form a gate electrode on the SAM that is a substantially uniform dense layer of GO-NPs; e) removing the patterned photoresist; and f) reducing the graphene oxide of the GO-NPs to form rGO-NPs. The substrate is typically a silicon oxide and the electrodes are typically gold. The gold electrodes may be formed on the silicon oxide substrate by conventional photolithography and lift-off.

Similar techniques are used to form the gate electrode. After the photoresist is applied, aminopropyltriethylsiloxane (APTES) and cysteamine SAMs are typically formed on exposed silicon oxide and gold surfaces, respectively, followed by centrifuging for one to ten minutes to apply a uniform dense layer of oppositely charged graphene encapsulated silicon oxide nanoparticles.

In an exemplary embodiment, the graphene encapsulated semiconductor nanoparticles are prepared by coating silicon oxide NPs with thin layers of graphene oxide (GO), which prevents aggregation and maintains high electrical conductivity. This may be achieved via the electrostatic interaction between the negatively charged GO and the positively charged silicon oxide NPs. A GO solution (e.g., 0.05 mg/ml in deionized water) is injected into a NP solution (e.g., 5 mg/ml), wherein the negatively charged GO assemble on the positively charged NP surface until equilibrium coverage is reached. Uniform assembly and saturation density of GO on the NP surface may be confirmed through transmission electron microscopy (TEM). In an embodiment, the GO thickness on the surface of the NPs is 5 nm, as measured from high resolution TEM. The NPs may be connected through a film of GO which may be reduced, i.e. with hydrazine, to form reduced GO (rGO) and used as an electrical carrier. For efficient use of NP junctions as electrical channels, it is desirable to assemble the NPs with high density on the device.

In a preferred embodiment, modified self-assembly methods (utilizing centrifugation) permit the assembly of NPs with high density in a short span using minimal amounts and concentrations of the NP solution. The high surface-to-volume ratio of the GO-encapsulated NPs generates three dimensional (3-D) electrical surfaces that significantly enhance detection limits and enable label-free, highly reproducible detection of clinically important biomarkers, such as HER2 and EGFR biomarkers for breast cancer, for example.

Figure 1B:
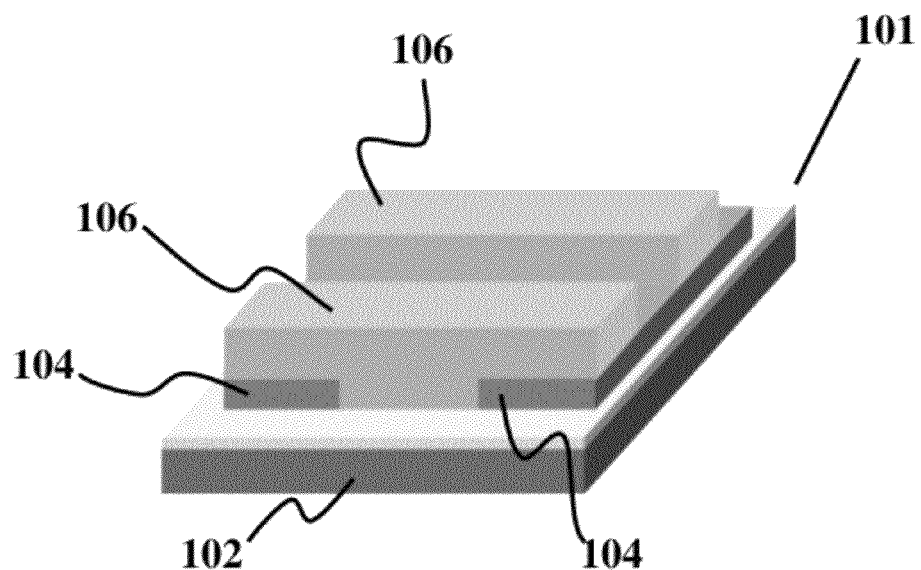

An advantageous aspect of an embodiment graphene-encapsulated NP biosensor is its ease of fabrication and measurement. The embodiment device may be fabricated using photolithography, followed by a lift-off process, by methods known in the art. See, e.g., Myung et al. *Adv. Mater.* 2010, 22, 2045; and Myung et al, *Adv. Mat.* 2005, 17, 2361. Referring now to FIGS. 1A-D, an exemplary process for manufacturing a reduced graphene oxide encapsulated nanopartile (rGO-NP) based field effect transistor (FET) biosensor 101 is provided. In one embodiment, gold electrodes 104 are first generated on a silicon dioxide substrate 102 using photolithography and lift-off, as shown in FIG. 1A. Referring now to FIG. 1B, a photoresist 106 is patterned on the substrate and electrodes using photolithography.

The exposed silicon oxide surface and gold surface are functionalized, for example, with self assembled monolayers (SAMs) of positively charged 3-aminopropyltriethoxysilane (APTES) and cysteamine, respectively (not shown). The SAM formation promotes the assembly of the negatively charged GO-NPs through electrostatic interactions. A uniform assembly of GO-NPs on the positively charged SAMs is obtained through centrifugation.

Figure 1C:
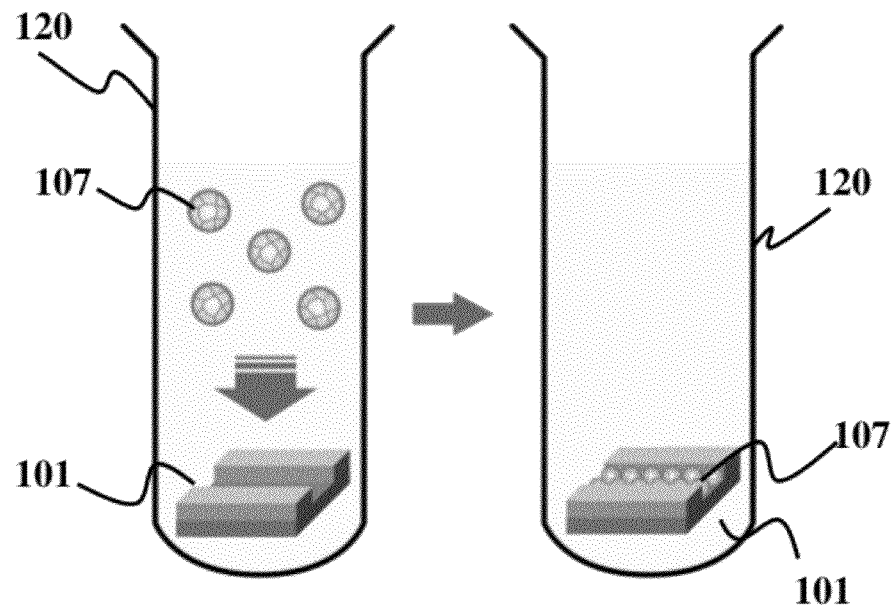
Figure 1D:
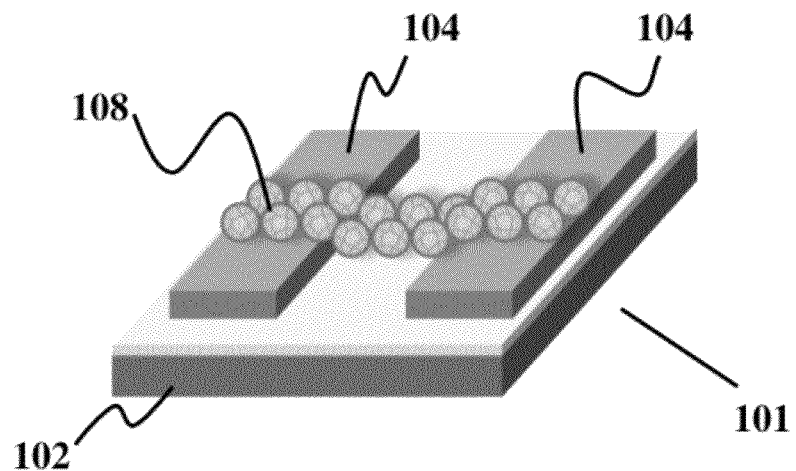

Referring now to FIG. 1C, the device 101 containing the patterned photoresist along with the SAMs is centrifuged in a solution of GO-NPs 107 at, for example, 2000 RPM for three minutes in a centrifuge tube. Despite a low concentration of GO-NPs 107, this method achieves uniform films of GO-NPs 107 having a high density in a reproducible manner over a large area, in a short time span. As shown in FIG. 1D, a uniform GO-NP 108 array can be generated by removing the patterned photoresist using an appropriate solvent, for example, acetone (not shown). The removal of photoresist does not disturb the GO-NP assembly 108. To render the insulating GO coating of the GO-NP assembly 108 electrically conductive, the GO is reduced, for example, through an overnight exposure to hydrazine vapor. The above described embodiments of methods of fabric-ating biosensor devices 101 can be integrated with conventional microfabrication processes, rendering the biosensor device 101 cost effective and relatively easy to produce on a large scale.

Once a biosensor device 101 containing the rGO-NP array is fabricated as described above, the selective detection of biomarkers may be was carried out by functionalizing the rGO-NPs with polypeptide binding partners that specifically bind to a biomarker of interest. For example, the polypeptide binding partners may be monoclonal antibodies (mAbs) against HER2 or EGFR. The bioconjugation may be achieved by methods known in the art. See, for example, Patolsky et al., *Nat. Protoc.* 2006, 1, 1711; and Zheng et al, *Nat. Biotechnol.* 2005, 23, 1294.

Figure 2A:
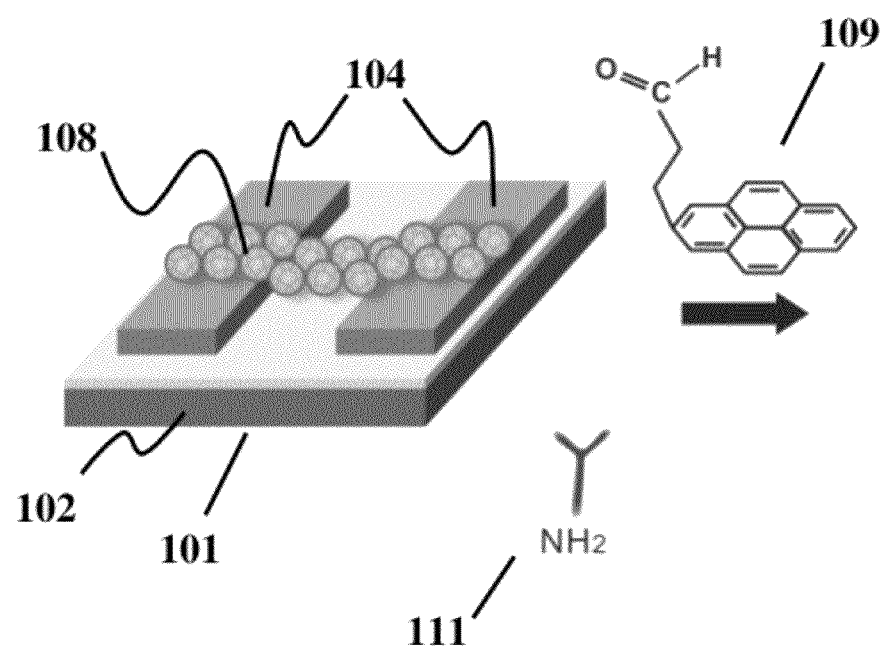
FIGS. 2A-C illustrates preparation of a device for real-time detection of a cancer marker according to the present invention and binding of a biomarker to a monoclonal antibody immobilized on the surface of the device.
Figure 2B:
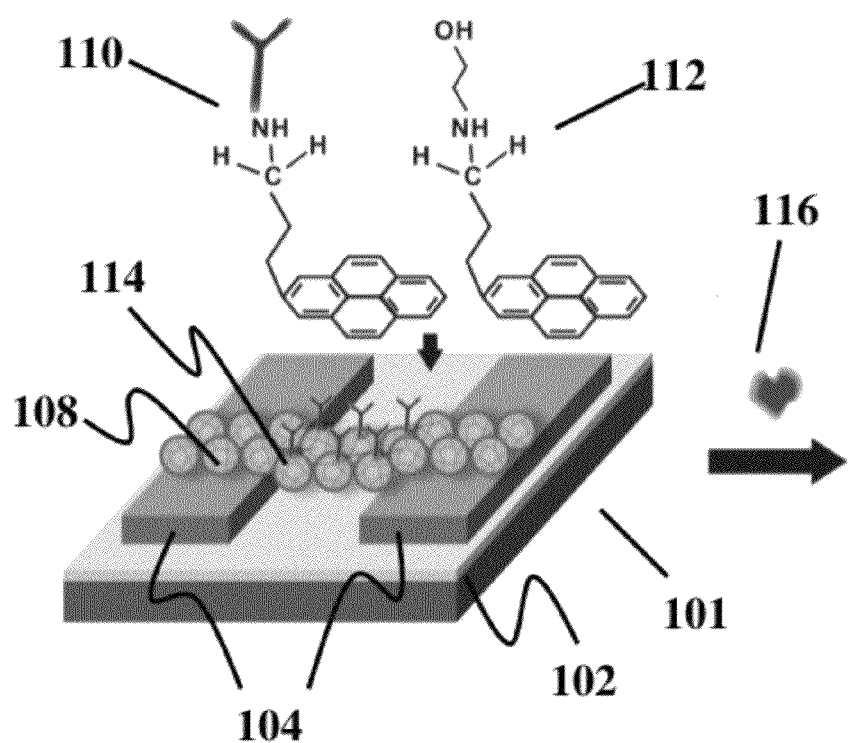

Referring to FIG. 2A, the reduced GO assembly 108 can be functionalized with an aldehyde compound 109, for example 4-(pyren-1-yl)butanal, in which the pyrene polyaromatic hydrocarbon portion of the aldehyde compound bonds to graphene coated nanoparticles via π-π interactions. This functionalization may occur, for example, by incubating the biosensor device 101 in a methanol solution (1:500) of 4-(pyren-1-yl)butanal for 30 minutes. Referring now to FIG. 2B, aldehyde groups are covalently bonded to the amine groups 111 of a polypeptide binding partner, including for example a peptide, an antigen, or an antibody. In a preferred embodiment, the polypeptide binding partner is a monoclonal antibody. In an exemplary embodiment, amine groups 111 of monoclonal HER2 or EGFR antibodies (1:50) are coupled to the aldehyde groups of compound 109 through reductive amination in the presence of 4 mM sodium cyanoborohydride in PBS (pH 7.4) for two hours.

The flexibility of the chemical functionalization technique used in the present invention makes the disclosed devices useful for attaching any mAB with a reactive amino group. Because most antibodies have lysines, they can be attached to the device. The device can not only be used for cancer biology, but also to detect the presence of biomarkers in stem cell biology. For instance, to determine the extent of neuronal differentiation of neural stem cells (NSCs), a device according to the present invention can be functionalized with antibodies against specific neuronal markers (TuJ1, MAP2 etc.) and detect changes in the signal using the cell lysate. The device is very flexible to adaptation to any kind of protein bio-sensing, particularly of biomarkers, provided antibodies specific for the protein to be detected are available.

Referring again to FIG. 2B, unreacted aldehyde groups may be blocked through an appropriate passivation technique. For example the biosensor device may be exposed to 100 mM ethanolamine to prevent non-specific interactions of proteins with amine groups 111. The embodiment biosensor device 101 is rinsed to wash away excess ethanolamine, for example in a continuous flow of PBS, pH 7.4 for 10 min.

Figure 2C:
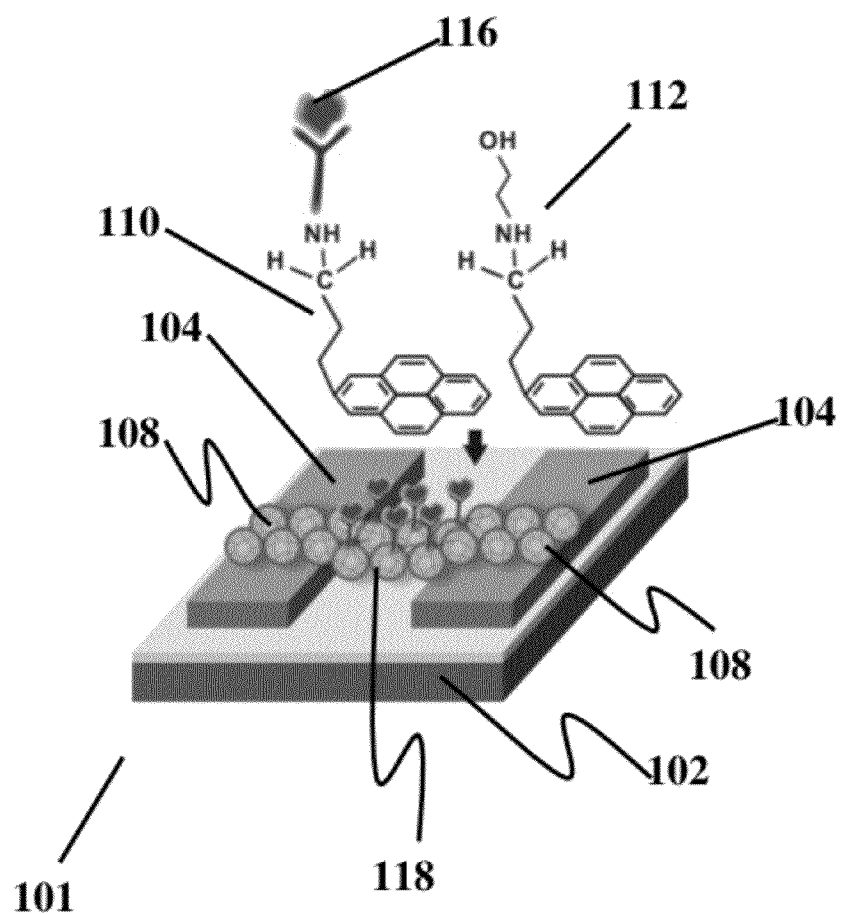

The surface chemistry used in the embodiment device plays a role in achieving highly selective and sensitive detection of protein biomarkers, for example biomarkers for HER2 or EGFR protein, the attachment of which to a monoclonal antibody against the biomarker that is immobilized on the device surface is shown in FIG. 2C. Furthermore, due to the large surface-to-volume ratio of the rGO-NPs, embodiment biosensors 101 are highly efficient as compared to the thin-film transistor-based biosensors.

In another embodiment, the present invention provides a method of detecting a biomarker in a sample. The present invention incorporates the discovery that the binding of the biomarkers to the binding partners induces positive potential gating effects that generate reduced hole density and reduced electrical conductance in the device. The decrease in conductance has proven concentration dependant to a one picomolar detection limit. The detection method therefore includes the steps of providing an FET of the invention that is functionalized with a linker coupled to a polypeptide binding partner for the biomarker to be detected, and that is in a circuit with a power source and a current measuring device; contacting the FET with a sample; and measuring any change in conductivity of the FET after contact with the sample, wherein a decrease in conductivity relative to a control is indicative of the presence of the biomarker in the sample.

Various embodiment graphene encapsulated NP-based biosensors 101 may be employed for highly selective and sensitive detection of biomarkers by using surface chemistry principles combined with nanomaterials and micro-/nanofabrication techniques. The three-dimensional structure of graphene encapsulated NP advantageously increases significantly the surface-to-volume ratio in FET-type biosensors, thereby improving the detection limits for target biomarkers, for example cancer biomarkers. In addition, the highly selective nature of embodiment biosensors 101 is shown as they can detect picomolar concentrations of target cancer biomarkers even in the presence of a highly concentrated BSA solution. The ease of fabrication and biocompatibility, along with excellent electrochemical and electrical properties of graphene nanocomposites, makes embodiment graphene encapsulated NP-based biosensors an ideal candidate for future biosensing applications within a clinical setting.

The following examples serve the further illustrate the present invention.

EXAMPLES

Example 1

Materials and Methods

Preparation of reduced graphene oxide and $SiO_2$ NPs: GO was obtained from SP-1 graphite utilizing the modified Hummer method. See, e.g., Eda et al., *Nat. Nanotechnol.* 2008, 3, 270. For the GO assembly on the surface of NPs, GO suspension was injected into the nanoparticle solution for 10 minutes, and GO-NPs were separated from GO solution using a centrifuge. $SiO_2$ NP (100 nm) solution was purchased from Corpuscular Inc. For GO-NP assembly, the photo resist-patterned substrate was placed in the NP solution, and GO-NPs were assembled on the substrate by applying centrifugal force for three minutes. After the deposition of GO-NPs on the substrate, the GO on the NP surface, having the low conductance, was reduced to graphene by exposure to hydrazine vapor overnight.

Surface molecular pattering: 3-Aminopropyltriethoxysilane (APTES) and cysteamine molecules were used in forming SAMs. For the patterning of APTES SAM on SiO2, the photoresist (AZ5214) was first patterned by photolithography using a short baking time (less than 10 min. in 95° C.). The patterned substrate was placed in the APTES solution (1:500 (v/v) in anhydrous hexane) for 7 min. For the patterning of APTES on the on $SiO_2$ layer, the substrate with photoresist patterns was placed in an APTES solution (1:500 (v/v) in anhydrous hexane) for 10 min. The photoresist was then removed with acetone.

Metal deposition and measurement of graphene devices: For electrode fabrication the photoresist was first patterned on the substrate. Ti/Au (10/30 nm) was then deposited on the substrate and the remaining photoresist was then removed with acetone for the lift-off process. A Keithley-4200 semiconductor parameter analyzer was used for measurement and data collection.

Synthesis of 1-butyl-3-methylimidazolium hexafluorophosphate (BMIM-$PF_6$). The BMIM-$PF_6$ was prepared according to a modified procedure reported by Dupont et al., *Org. Synth.* 2002, 79, 236. 72.5 mL (64.2 g, 0.69 mol) of 1-chlorobutane and 50 mL of 1-methylimidazole (51.8 g, 0.63 mol) were added to a dry round-bottom flask fitted with a reflux condenser and a magnetic stirring bar. The reaction mixture was stirred at 80° C. for 48 h. The unreacted 1-chlorobutane was evaporated at reduced pressure. 1-methylimidazole was washed three times by adding a small amount of ethyl acetate to the mixture and decanted.

1-butyl-3-methylimidazolium chloride (BMIM-Cl) was obtained by evaporating the remaining ethyl acetate at reduced pressure and drying in a vacuum oven. 69.6 g (0.38 mol) of $KPF_6$ and 150 mL of $H_2O$ were added into a round-bottom flask, followed by the addition of 50 mL (0.32 mol) of as-prepared BMIM-Cl. After vigorous stirring for 24 h at room temperature, undissolved $KPF_6$ disappeared and two phases formed. The lower ionic liquid layer was separated and dissolved in 50 mL dichloromethane. The dichloromethane solution was washed with water until no chloride ($Cl^-$) anion in the water layer could be detected by $AgNO_3$ solution. Dichloromethane was evaporated and 1-butyl-3-methylimidazolium hexafluorophosphate (BMIM-$PF_6$) was obtained as colorless or slightly yellow viscous liquid after drying in a vacuum oven.

The synthesized BMIM-$PF_6$ was analyzed with $^1H$ NMR. Spectra were recorded at 600 MHz. The following chemical shifts reported in ppm downfield to TMS ($\delta$=0 ppm) were observed: $^1H$ NMR (600 MHz, DMSO-$D_6$): $\delta$ 0.91(t, 3H), $\delta$ 1.27(m, 2H), $\delta$ 1.77(m, 2H), $\delta$ 3.85(s, 3H), $\delta$ 4.16(t, 2H), $\delta$ 7.67(s, 1H), $\delta$ 7.74(s, 1H), $\delta$ 9.08(s, 1H).

Synthesis of 4-(pyren-1-yl)butanal. 10 mL of methylene chloride was added to 1.097 g (4 mmol) of 4-(pyren-1-yl) butyl alcohol and stirred vigorously at room temperature for 10 min hour. The reaction was followed by addition of 1.292 g (1.5 Eq.) of PCC (Pyridinium chlorochromate) in 10 mL methylene chloride and the reaction mixture was stirred for 2 h. The reaction mixture was then diluted with 5 volumes of anhydrous ether (100 mL) and washed with 1:1 brine:water, saturated aq. $Na_2SO_3$ solution, and brine, respectively, dried over anhydrous $Na_2SO_4$ and concentrated to give the aldehyde. The crude product was purified by silica gel flash chromatography (hexanes: ethyl acetate, 9:1, rf: 0.4) to yield 1.06 g (97%). Most of the crude products were very clean and could be used directly for further applications.

Example 2

The following example illustrates the fabrication and application of a reduced graphene oxide (rGO) encapsulated nanoparticle (NP)-based FET biosensor for selective and sensitive detection of key biomarker proteins for breast cancer. This example demonstrates the use of Human Epidermal growth factor Receptor 2 (HER2) and Epidermal Growth Factor Receptor (EGFR), which are known to be over-expressed in breast cancers, as examples to demonstrate the high sensitivity and selectivity of the graphene-encapsulated NP biosensor. This biosensor could be used to detect any biomarkers with relative ease. In typical experiments for fabricating the graphene encapsulated NPs-based biosensors, individual silicon oxide NPs (100 nm), functionalized with 3-aminopropyltriethoxysilane (APTES), were first coated with thin layers of graphene oxide (GO), which prevent aggregation and maintain high electrical conductivity (FIG. 1). This was mainly achieved via the electrostatic interaction between the negatively charged GO and the positively charged silicon oxide NPs. The GO solution (0.05 mg/ml in deionized water) was simply injected into the NP solution (5 mg/ml), wherein the negatively charged GO assembled on the positively charged NP surface until equilibrium coverage was reached.

The transmission electron microscopy (TEM) image of the GO-coated NPs clearly showed the uniform assembly and saturation density of GO on the NP surface. The GO thickness on the surface of the NPs was 5 nm, as measured from HR-TEM. The NPs were connected through a film of GO which was used as an electrical carrier after its reduction to rGO. For efficient use of NP junctions as electrical channels, it was important to assemble the NPs with high density on the device. The scanning electron microscopy (SEM) images showed well-defined, dense rGO-NP patterns uniformly covering a large area of the silicon oxide substrate.

Furthermore, the modified self-assembly method (utilizing centrifugation) allowed assembly of NPs with high density in a short span and by using minimal amount and concentration of the NP solution. The high surface-to-volume ratio of the GO-encapsulated NPs generated 3-D electrical surfaces that significantly enhanced detection limits and enabled label-free, highly reproducible detection of clinically important cancer markers.

The device was fabricated using photolithography, followed by a lift-off process. See, e.g., Myung et al. Adv. Mater. 2010, 22, 2045; and Myung et al., Adv. Mat. 2005, 17, 2361. First gold electrodes were generated on a silicon oxide substrate using photolithography and lift-off. To generate arrays of GO-NPs, the photoresist (AZ 5214) was patterned on the substrates with gold electrodes using photolithography. The exposed silicon oxide surface and gold surface were functionalized with self assembled monolayers (SAMs) of positively charged 3-aminopropyltriethoxysilane (APTES) and cysteamine, respectively.

The SAM formation promoted the assembly of the negatively charged GO-NPs (through electrostatic interactions). A relatively simple technique involving centrifugation was employed for the uniform assembly of GO-NPs on the positively charged SAMs. In this technique, the substrate containing the patterned photoresist along with the SAMs was centrifuged in a solution of GO-NPs at 2000 RPM for 3 min in a centrifuge tube. Despite a low concentration of GO-NPs, uniform films of NPs having a high density were achieved in a reproducible manner. This is in stark contrast to the standard methods used for assembling NPs on surfaces. Other methods generally rely on using larger volumes of solution containing higher concentrations of NPs, where contact of the NPs with the surface is mainly made through infrequent Brownian motion, which eventually causes the NP assembly.

On the other hand, the present centrifugation technique achieved uniform, highly dense layers of graphene-encapsulated NPs over a large area, in a short time span. A uniform NP array was then generated by removing the patterned photoresist using acetone. The removal of photoresist did not disturb the assembly of GO-NPs. To render the insulating GO electrically conductive, the GO was reduced through an overnight exposure to hydrazine vapor. This method of fabricating the device is very powerful as it can be integrated with conventional micro-fabrication processes, which makes the device cost effective and relatively easy to produce on a large scale.

One of the key barriers of using graphene FET-based biosensors is to operate the device at physiological conditions (e.g. different pH and salt concentrations), in which different ionic environments affect the conductivity of graphene FET-based biosensors. To study the working conditions of the present graphene FET-based biosensors in aqueous solutions, the gating effect of the rGO-NP-based biosensor was measured using an ionic liquid gate. A typical source-drain current vs. gate potential plot was obtained in an ionic liquid, 1-butyl-3-methylimidazolium tetrafluoroborate (BmimPF$_6$) (See Example 1 hereinabove for the synthesis of BmimPF$_6$). In an ionic liquid, the high concentration of ions renders the thickness of the diffusion layer negligible, thus making it useful as a gate insulating layer. Silver (Ag) wire was used as the reference electrode for the measurements in the ionic liquid. The gating effect observed in the GO-NP devices was similar to that observed in rGO thin-film transistors that have ambipolar conduction and p-type behavior near zero gate voltage. In the present case, the top-gate bias was swept with ~0.05V/sec sweep speed under the source-drain bias of 0.5V.

Once the device, containing the rGO-NP array, was optimized for biosensing, the selective detection of HER2 and EGFR was carried out by functionalizing the rGO-NPs with monoclonal antibodies (mAbs) against HER2 or EGFR. The bioconjugation chemistry is known in the art and involved three basic steps. See, e.g. Patolsky et al., Nat. Protoc. 2006, 1, 1711; and Zheng et al., Nat. Biotechnol. 2005, 23, 1294. First, the reduced GO surface was functionalized with 4-(pyren-1-yl)butanal via π-π interactions by incubating the device in a methanol solution (1:500) of 4-(pyren-1-yl)butanal (See Example 1 for synthesis) for 30 min (FIG. 2A). Second, the aldehyde groups were coupled to the amine groups of the monoclonal HER2 or EGFR antibodies (1:50) through reductive amination in the presence of 4 mM sodium cyanoboro-hydride in PBS (pH 7.4) for two hours (FIG. 2B). Third, unreacted aldehyde groups were blocked using 100 mM ethanolamine in a similar manner to prevent non-specific interactions of proteins. Finally, the device was rinsed in a continuous flow of PBS (pH 7.4) for 10 min. The surface chemistry used in the device plays a crucial role in achieving highly selective and sensitive detection of HER2 or EGFR protein (FIG. 2C). Furthermore, due to the large surface-to-volume ratio of the rGO-NPs, the present biosensors were highly efficient as compared to the thin-film transistor-based biosensors.

The sensitivity of the rGO-NP devices, functionalized with HER2 mAbs, was determined by measuring the changes in conductance as the solution concentration of HER2 was varied from 10 fM to 1 µM. In all experiments, only 1 µL, of each solution was added onto the device. Representative time-dependent data showed that on the addition of a 10 fM solution of HER2, no change in conductance was observed. However on increasing the concentration to 1 pM, a decrease in conductance of the p-type rGO-NP device was observed due to the binding of HER2 to the mAbs. As the concentrations of the solutions were subsequently increased, a concentration dependent decrease in the conductance of the rGO-NP device was observed. Thus, the detection limit of the biosensor was observed to be 1 pM in a solution containing only HER2 protein, which is a significant improvement over thin-film-transistor-type sensors based on the graphene. The observed change in electrical conductivity can be attributed to the p-type characteristic of the rGO-NP FET-based sensors as the amine groups on the protein surface are positively charged. Binding of these positively charged target-biomolecules such as HER2 or EGFR to the rGO surface induces positive potential gating effects that generate reduced hole density and electrical conductance.

Figure 3A:
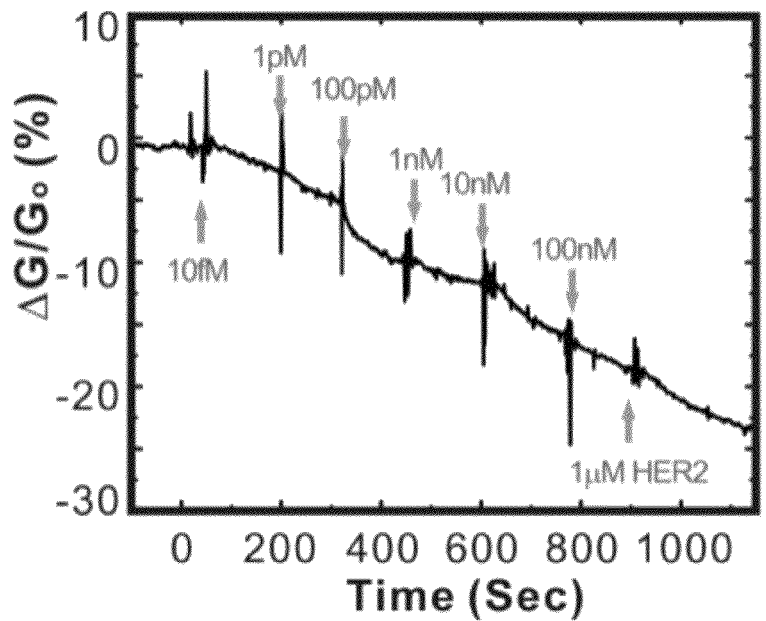
FIGS. 3A-C are graphs that show the sensitivity of biosensors according to the present invention.

To test the selectivity of the graphene FET-based biosensors, the selective detection of the device was investigated in competitive binding studies with bovine serum albumin (BSA) FIG. 3A depicts relative conductance change (%) in response to the concentration of HER2 with $V_{DS}$=1V and $V_g$=0V. Time-dependent conductance measurements recorded on the rGO-NP devices, functionalized with HER2 mAbs, showed no change in conductance on adding PBS, and 50 µg/ml BSA. However, on adding 1 µL of 100 pM solution of HER2 to the BSA solution on the device, a rapid and sharp change in conductance was observed, demonstrating the high selectivity of the device. On adding the 1 µM solution of HER2, the conductance further decreased rapidly and drastically. In spite of the presence of a solution having a very high concentration of BSA (50 µg/ml), the detection limit of the target protein, HER2, was 100 pM, which clearly demonstrates the remarkable sensitivity and selectivity of our rGO-NP biosensor.

Figure 3B:
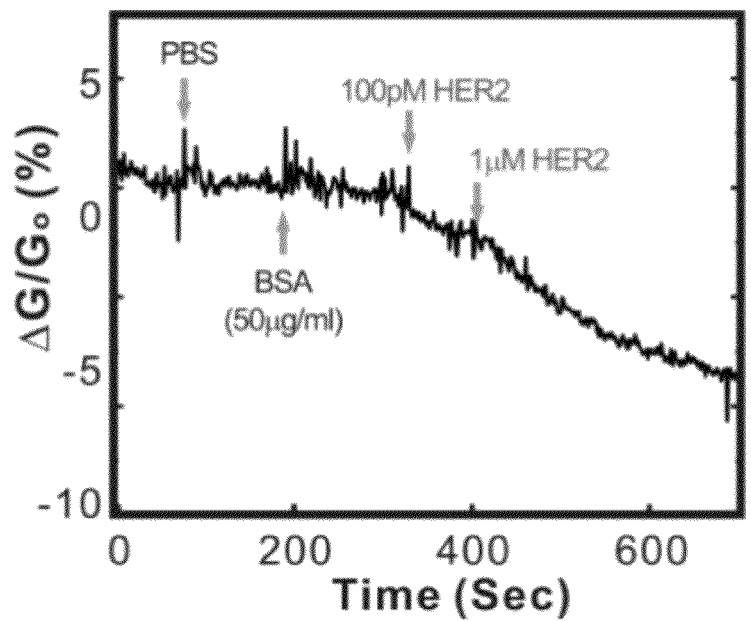

FIG. 3B shows the sensitivity (relative conductance change) of the biosensor as a function of the HER2 concentration. The lowest HER2 concentration level that can be detected is 1 pM which showed a decrease in conductance (3.9%). Similar to the non-linear behavior of CNT FET-based sensors, the present sensor responses increased non-linearly with the increase in the HER2 concentration from 1 pM, which clearly shows that the sensor response is due to the binding of HER2 to the HER2 mAbs. FIG. 3B shows the selectivity of the biosensor in response to PBS buffer, BSA with 50 µg/ml and HER2 (100 pM and 1 µM).

Figure 3C:
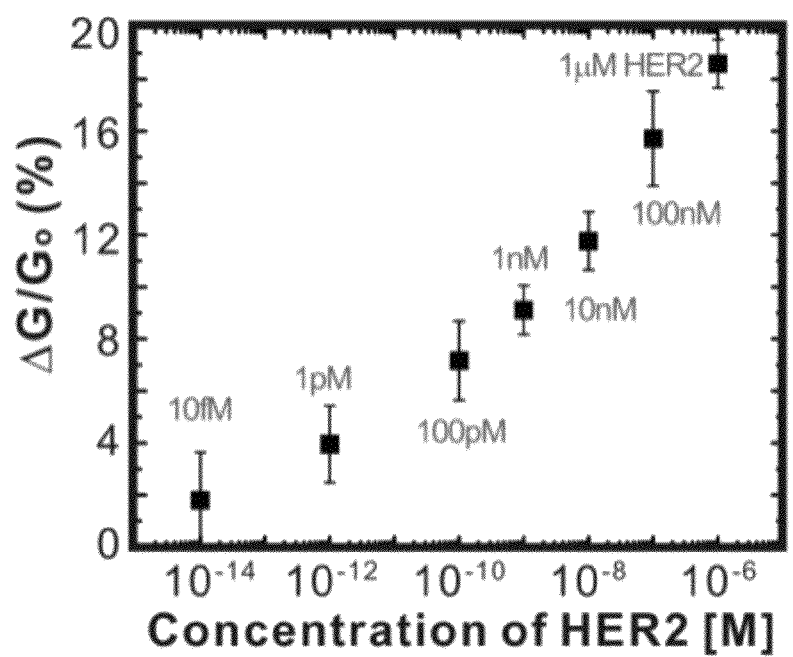

FIG. 3C shows sensor sensitivity (relative conductance change, %) as a function of the HER2 concentration with $V_{DS}=1V$ and $V_g=0V$, wherein all experiments were performed multiple times (n=30) to collect statistical data (with error bars) and confirm the reproducibility and robustness of an embodiment biosensing system.

In addition to HER2, the sensitivity and selectivity of the device for detecting EGFR was investigated. The device was functionalized with EGFR mAbs and the change in conductance on the addition of EGFR solution was observed. The trend in conductance change was similar to that observed with HER2, with the detection limit being 100 pM for EGFR, and 10 nM in the presence of BSA (50 µg/ml). The slight decrease in sensitivity for detecting EGFR (relative to HER2) might be due to the difference in binding affinities of the two mAbs to their respective proteins. However, the result demonstrates the capacity of the present biosensors to detect different biomarkers in a sensitive and selective manner.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A field effect transistor (FET) comprising a source electrode and a drain electrode distanced apart from each other on a semi-conductor substrate, and a gate electrode consisting of a uniform layer of reduced graphene oxide encapsulated semiconductor nanoparticles (rGO-NPs), wherein said gate electrode is disposed between and contacts both the source and drain electrodes.

2. The FET of claim 1, wherein the semiconductor nanoparticles comprise silicon oxide nanoparticles.

3. The FET of claim 1, wherein the rGO-NPs are functionalized with a binding partner for a biomarker.

4. The FET of claim 3, wherein the binding partner for a biomarker is bonded to the rGO-NPs by a linker molecule having the structure:

X—Y—Z wherein X is a polyaromatic ring structure that bonds non-covalently with the GO-NPs; Y is a spacer moiety selected from the group consisting of alkylene and poly(alkylene oxide) groups containing from 1 to 12 carbon atoms; and Z is an omega-functional group capable of reacting with, or being activated to react with, and covalently bonding to an amine.

5. The FET of claim 4, wherein said polyaromatic ring structure comprises a structure found in a polyaromatic hydrocarbons selected from the group consisting of pyrene, anthracene, phenanthrene, benzopyrene, coronene and triphenylene.

6. The FET of claim 4, wherein the spacer moiety, Y, is selected from the group consisting of alkylene groups containing from three to six carbon atoms.

7. The FET of claim 4, wherein the omega functional group, Z, is an aldehyde, ketone or carboxylic acid group.

8. The FET of claim 3, wherein the binding partner is selected from the group consisting of antigens, antibodies and antibody fragments.

9. The FET of claim 8, wherein the binding partner is a monoclonal antibody.

10. The FET of claim 9, wherein the monoclonal antibody is a monoclonal antibody against a neuronal or cancer biomarker.

11. The FET of claim 10, wherein the cancer biomarker is Human Epidermal growth factor Receptor 2 (HER2) or Epidermal Growth Factor Receptor (EGFR).

12. The FET of claim 10, wherein the neuronal biomarker is TuJ1 or MAP2.

13. A method of manufacturing a field effect transistor (FET), the method comprising:
   layering a pair of conductive metal electrodes on a semi-conductor substrate;
   layering a patterned photoresist on the substrate and electrodes to define an exposed area for formation of a gate electrode;
   functionalizing the semiconductor and metal electrode surfaces on the exposed area with a self assembled monolayer (SAM) of positively charged amines; and
   centrifuging the functionalized substrate in a solution comprising graphene oxide-encapsulated semiconductor nano-particles (GO-NPs) to form a graphene gate electrode on the SAM that is a substantially uniform layer of GO-NPs disposed between and contacting both electrodes.

14. The method of claim 13, further comprising the steps of removing the patterned photoresist and reducing the graphene oxide of the GO-NPs to form rGO-NPs vapor.

15. The method of claim 14, further comprising the steps of functionalizing the rGO-NP with a linker molecule having the structure:

X—Y—Z wherein X is a polyaromatic ring structure that bonds non-covalently with the GO-NPs; Y is a spacer moiety selected from the group consisting of alkylene and poly(alkylene oxide) groups containing from 1 to 12 carbon atoms; and Z is an omega-functional group capable of reacting with, or being activated to react with, and covalently bonding to an amine; and
   covalently bonding the omega functional group of the linker molecule to the amine groups of a binding partner for a biomarker.

16. The method of claim 15, wherein said binding partner is selected from the group consisting of antigens, antibodies and antibody fragments.

17. The method of claim 16, wherein the binding partner is a monoclonal antibody against a cancer biomarker selected from Human Epidermal growth factor Receptor 2 (HER2), Epidermal Growth Factor Receptor (EGFR) or a neuronal biomarker selected from TuJ1 and MAP2.

18. A method of detecting a biomarker is a sample, comprising:
   introducing a sample to a surface of a gate electrode of a field effect transistor (FET) biosensor according to claim 1, wherein said gate electrode has bonded thereto a binding partner for said biomarker; and
   measuring a current in a channel region between a source electrode and a drain electrode of the FET biosensor before and after introducing said sample;

wherein a reduction in said current is indicative of the presence of said biomarker in said sample.

19. The method of claim 18, wherein said binding partner is selected from the group consisting of antigens, antibodies and antibody fragments.

20. The method of claim 19, wherein the binding partner is a monoclonal antibody against a cancer biomarker selected from Human Epidermal growth factor Receptor 2 (HER2), Epidermal Growth Factor Receptor (EGFR) or a neuronal biomarker selected from TuJ1 and MAP2.

* * * * *